(12) United States Patent
Hori (10) Patent No.: US 11,878,130 B2
(45) Date of Patent: *Jan. 23, 2024

(54) CATHETER COIL WITH TAPERED DISTAL JOINT PART

(71) Applicant: ASAHI INTECC CO., LTD., Seto (JP)

(72) Inventor: Takayuki Hori, Seto (JP)

(73) Assignee: ASAHI INTECC CO., LTD., Seto (JP)

(*) Notice: Subject to any disclaimer, the term of this patent is extended or adjusted under 35 U.S.C. 154(b) by 0 days.

This patent is subject to a terminal disclaimer.

(21) Appl. No.: 17/749,455

(22) Filed: May 20, 2022

(65) Prior Publication Data

US 2022/0273912 A1 Sep. 1, 2022

Related U.S. Application Data

(63) Continuation of application No. 16/937,056, filed on Jul. 23, 2020, now Pat. No. 11,369,774, which is a
(Continued)

(51) Int. Cl.
*A61M 25/01* (2006.01)
*A61M 25/00* (2006.01)
*A61M 25/09* (2006.01)

(52) U.S. Cl.
CPC .... *A61M 25/0138* (2013.01); *A61M 25/0023* (2013.01); *A61M 25/0053* (2013.01);
(Continued)

(58) Field of Classification Search
CPC ............ A61M 25/0067; A61M 25/001; A61M 25/008; A61M 25/0069; A61M 25/0068;
(Continued)

(56) References Cited

U.S. PATENT DOCUMENTS 5,664,580 A * 9/1997 Erickson ............... A61M 25/09
128/877
5,700,253 A * 12/1997 Parker ............... A61M 25/0012
604/524
(Continued)

FOREIGN PATENT DOCUMENTS

CN 101920056 A 12/2010
CN 104053471 A 9/2014
(Continued)

OTHER PUBLICATIONS

Overview of materials for Stainless Steel, www.matweb.com/search/DataSheet.aspx?MatGUID=71396e57ff5940b791ece120e4d563e0, 2 pp. (2023, Matweb LLC) (accessed Jun. 26, 2023) (Year: 2023).*
(Continued)

*Primary Examiner* — Jason E Flick
*Assistant Examiner* — Adam J. Cermak
(74) *Attorney, Agent, or Firm* — Oliff PLC (57) ABSTRACT

A catheter includes a hollow shaft having a tip part decreasing in diameter in a direction of a distal end, and a coil body covering the hollow shaft. The tip part has a small diameter portion, a large diameter portion, and a tapered portion gradually increasing in diameter from the small diameter portion toward the large diameter portion. The coil body has a substantially cylindrical joint part at which an end portion of the coil body in the direction of the distal end is joined in the circumferential direction. The joint part is located over the tapered portion and/or the small diameter portion, and in a state in which the hollow shaft extends substantially linearly, the distance between an inner peripheral surface of the joint part and outer peripheral surfaces of the tapered portion and/or the small diameter portion increases in the direction of the distal end.

15 Claims, 6 Drawing Sheets

Related U.S. Application Data continuation of application No. PCT/JP2018/002562, filed on Jan. 26, 2018.

(52) U.S. Cl.
CPC ... *A61M 25/09* (2013.01); *A61M 2025/09083* (2013.01); *A61M 2205/0216* (2013.01)

(58) Field of Classification Search
CPC ............ A61M 25/0053; A61M 25/005; A61M 25/0045; A61M 25/0023; A61M 2025/1093; A61M 2025/09175; A61M 2025/0081; A61M 2205/0216
See application file for complete search history.

(56) References Cited

U.S. PATENT DOCUMENTS

| | | | | |
|---|---|---|---|---|
| 5,769,830 | A * | 6/1998 | Parker | A61M 25/0069 604/528 |
| 6,113,557 | A * | 9/2000 | Fagan | A61M 25/09 600/585 |
| 6,183,420 | B1 * | 2/2001 | Douk | A61M 25/09 600/585 |
| 7,322,944 | B2 * | 1/2008 | Osawa | A61M 25/09 600/585 |
| 7,909,779 | B2 * | 3/2011 | Shimogami | A61M 25/0012 72/135 |
| 7,985,213 | B2 * | 7/2011 | Parker | A61M 25/005 604/526 |
| 8,540,695 | B2 * | 9/2013 | Shimogami | A61M 25/005 604/525 |
| 8,622,933 | B2 * | 1/2014 | Maki | A61M 25/09 600/585 |
| 8,814,890 | B2 * | 8/2014 | Miyata | A61M 25/0082 606/159 |
| 9,028,428 | B2 * | 5/2015 | Maki | A61M 25/09 600/585 |
| 9,339,629 | B2 * | 5/2016 | Watanabe | A61M 25/005 |
| 9,717,884 | B2 * | 8/2017 | Matsumoto | A61M 25/0045 |
| 10,166,363 | B2 * | 1/2019 | Yagi | A61M 25/008 |
| 10,245,412 | B2 * | 4/2019 | Shimizu | A61M 25/0052 |
| 10,258,767 | B2 * | 4/2019 | Shimizu | A61M 25/0052 |
| 10,493,234 | B2 * | 12/2019 | Kanazawa | A61M 25/005 |
| 10,912,921 | B2 * | 2/2021 | Hanaoka | A61M 39/10 |
| 10,940,293 | B2 * | 3/2021 | Kubo | A61M 25/005 |
| 11,096,703 | B2 * | 8/2021 | Panian | A61M 25/0082 |
| 2009/0018525 | A1 * | 1/2009 | Waite | A61M 25/008 604/104 |
| 2010/0094258 | A1 * | 4/2010 | Shimogami | A61M 25/005 606/191 |
| 2010/0318065 | A1 | 12/2010 | Miyata et al. | |
| 2011/0106056 | A1 * | 5/2011 | Hatano | A61M 25/0052 604/527 |
| 2011/0245775 | A1 * | 10/2011 | Tekulve | A61M 25/0045 264/171.12 |
| 2012/0059279 | A1 * | 3/2012 | Kawasaki | A61L 31/022 600/585 |
| 2012/0089127 | A1 | 4/2012 | Miyata et al. | |
| 2012/0179141 | A1 | 7/2012 | Miyata et al. | |
| 2012/0310213 | A1 * | 12/2012 | Kronfeld | A61M 25/001 604/529 |
| 2014/0309533 | A1 | 10/2014 | Yamashita et al. | |
| 2015/0231360 | A1 * | 8/2015 | Watanabe | A61M 25/0021 604/523 |
| 2015/0273182 | A1 * | 10/2015 | Watanabe | A61M 25/0069 604/527 |
| 2015/0306347 | A1 * | 10/2015 | Yagi | A61M 25/0138 604/524 |
| 2016/0151078 | A1 * | 6/2016 | Kanazawa | A61M 25/001 606/159 |
| 2016/0235941 | A1 * | 8/2016 | Matsumoto | A61M 25/005 |
| 2016/0279383 | A1 * | 9/2016 | Kanazawa | A61M 25/001 |
| 2017/0072165 | A1 * | 3/2017 | Lim | A61M 25/0053 |
| 2017/0113018 | A1 * | 4/2017 | Shimizu | A61M 25/005 |
| 2018/0056037 | A1 * | 3/2018 | Shimizu | A61M 25/008 |
| 2019/0275290 | A1 | 9/2019 | Yamashita et al. | |
| 2019/0381278 | A1 * | 12/2019 | Hori | A61M 25/0045 |
| 2020/0129730 | A1 * | 4/2020 | Ishikawa | A61M 25/0068 |
| 2020/0353210 | A1 * | 11/2020 | Hori | A61M 25/0053 |
| 2022/0257901 | A1 * | 8/2022 | Kuboki | A61M 25/0045 |

FOREIGN PATENT DOCUMENTS

| | | | |
|---|---|---|---|
| CN | 105013061 A | 11/2015 | |
| EP | 2005988 B1 | 3/2016 | |
| EP | 2005988 B1 * | 3/2016 | ............ A61M 25/09 |
| JP | 2003-520651 A | 7/2003 | |
| JP | 2012-147956 A | 8/2012 | |
| JP | 2015-181787 A | 10/2015 | |
| JP | 2016152907 A | 8/2016 | |
| JP | 2016152907 A * | 8/2016 | ........ A61M 25/0012 |
| JP | 2016-179170 A | 10/2016 | |
| JP | 2019-37572 A | 3/2019 | |
| JP | 2019037572 A * | 3/2019 | ............ A61M 25/00 |
| WO | 9426337 A1 | 11/1994 | |
| WO | WO-9426337 A1 * | 11/1994 | ........... A61L 31/022 |
| WO | 9711738 A1 | 4/1997 | |
| WO | WO-9711738 A1 * | 4/1997 | ............ A61M 25/09 |
| WO | 9732518 A1 | 9/1997 | |
| WO | WO-9732518 A1 * | 9/1997 | ........... A61B 5/0215 |
| WO | 9919017 A1 | 4/1999 | |
| WO | WO-9919017 A1 * | 4/1999 | ............ A61M 25/09 |
| WO | 01/54761 A2 | 8/2001 | |
| WO | 2012158152 A1 | 11/2012 | |
| WO | WO-2012158152 A1 * | 11/2012 | ......... A61B 1/00087 |
| WO | 20 19026220 A1 | 2/2019 | |
| WO | WO-2019026220 A1 * | 2/2019 | .......... A61M 25/001 |
| WO | 2021090821 A1 | 5/2021 | |
| WO | WO-2021090821 A1 * | 5/2021 | ........ A61M 25/0045 |

OTHER PUBLICATIONS

Overview of materials for Gold Alloy, www.matweb.com/search/DataSheet.aspx?MatGUID=b9639c2f4ed84006923b2956f90cc13c &ckck=1 , 2 pp. (2023, Matweb LLC) (accessed Apr. 3, 2023) (Year: 2023).*

Overview of materials for Thermoset Polyurethane, Elastomer, Unreinforced, www.matweb.com/search/DataSheet.aspx?MatGUID= 26606798bc9d4538a7c7eadf78ab082b&ckck=1 , 2 pp. (2023, Matweb LLC) (accessed Apr. 3, 2023) ("MatWeb PU") (Year: 2023).*

Hardness Conversion Chart, www.carbidedepot.com/formulas-hardness.htm ; 3 pp. (2023, Carbide Depot, Inc.) (accessed Jun. 27, 2023) (Year: 2023).*

* cited by examiner

CATHETER COIL WITH TAPERED DISTAL JOINT PART

CROSS REFERENCE TO RELATED APPLICATIONS

This application is a continuation of U.S. application Ser. No. 16/937,056 filed Jul. 23, 2020 (issued as U.S. Pat. No. 11,369,774 on Jun. 28, 2022), which is a continuation application of International Application No. PCT/JP2018/002562, filed Jan. 26, 2018. The contents of the applications is incorporated herein by reference in its entirety.

BACKGROUND

The disclosed embodiments relate to a catheter.

For example, when treating an abnormality in a blood vessel such as chronic total occlusion (CTO), after first passing a guide wire through the blood vessel to be treated, a catheter is passed along the guide wire to a destination to perform the desired treatment.

As an example of such a catheter, Japanese Patent Document JP2012-147956 discloses a catheter in which a winding layer formed by winding wire materials into a coil shape is arranged on an outer peripheral surface of an inner layer that defines a main lumen through which a guide wire or the like is passed, and ring-shaped joining members are joined at fixed intervals on an outer periphery of the winding layer.

The above-described technique is excellent in that since the winding layer is joined with the joining members, it is possible to improve the torquability and ensure rotation of a tip part of the catheter by hand operation, and also prevent the coil-shaped wire materials forming the winding layer from unwinding.

SUMMARY

However, in the conventional catheter as described above, while it is possible to prevent unwinding of the wire materials, the joining between the joining members and the winding layer reduces the flexibility of the winding layer, and particularly, when passing the catheter through a blood vessel with a sharply curved shape, the ability to track the blood vessel may significantly decline.

The disclosed embodiments have been made based on the above circumstances, and an object thereof is to provide a catheter that enables a tip part of a hollow shaft to curve within a wide range while preventing unwinding of a coil body.

To achieve the above object, a catheter according to the disclosed embodiments includes: a hollow shaft including a tip part having an outer diameter gradually decreasing in a direction of a distal end; a coil body wound to cover an outer periphery of the hollow shaft; and a cover member covering the coil body and provided on the outer periphery of the hollow shaft. The tip part of the hollow shaft includes a small diameter portion that is a distalmost portion of the tip part, a large diameter portion having a larger outer diameter than the small diameter portion and located in a proximal end direction of the small diameter portion, and a tapered portion that is continuous with the small diameter portion and the large diameter portion and gradually increases in diameter from the small diameter portion toward the large diameter portion. The coil body includes a substantially cylindrical joint part at which an end portion of the coil body in the direction of the distal end is joined in the circumferential direction. The joint part is located over the tapered portion and/or the small diameter portion in the axial direction of the hollow shaft. In a state in which the hollow shaft extends substantially linearly, a distance between an inner peripheral surface of the joint part and outer peripheral surfaces of the tapered portion and/or the small diameter portion increases in the direction of the distal end.

In the present specification, the "distal direction" means a direction of the catheter axis in which the small diameter portion is located with respect to the large diameter portion of the hollow shaft. Further, the "proximal direction" means a direction of the catheter axis opposite to the distal direction.

DETAILED DESCRIPTION OF EMBODIMENTS

The catheter according to the present disclosure includes a hollow shaft including a tip part having an outer diameter gradually decreasing in a direction of a distal end, a coil body wound to cover an outer periphery of the hollow shaft, and a cover member covering the coil body and provided on the outer periphery of the hollow shaft. The tip part of the hollow shaft includes a small diameter portion that is a distalmost portion of the tip part, a large diameter portion having a larger outer diameter than the small diameter portion and located in a proximal end direction of the small diameter portion, and a tapered portion that is continuous with the small diameter portion and the large diameter portion and gradually increases in diameter from the small diameter portion toward the large diameter portion. The coil body includes a substantially cylindrical joint part at which an end portion of the coil body in the direction of the distal end is joined in the circumferential direction. The joint part is located over the tapered portion and/or the small diameter portion in the axial direction of the hollow shaft. In a state in which the hollow shaft extends substantially linearly, a distance between an inner peripheral surface of the joint part and outer peripheral surfaces of the tapered portion and/or the small diameter portion increases in the direction of the distal end.

Hereinafter, embodiments of the present invention will be described with reference to the drawings, but the present invention shall not be limited only to the embodiments described in the drawings.

Figure 1:
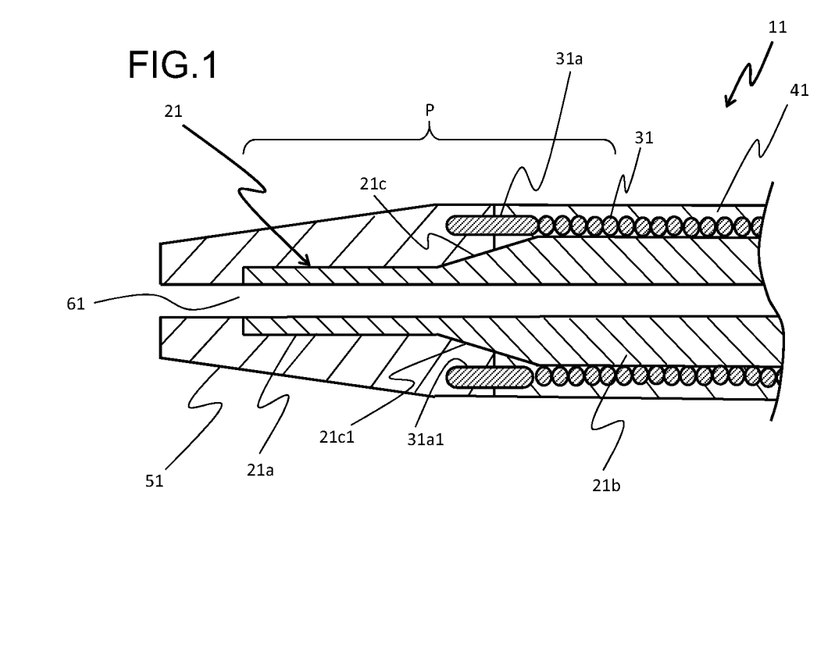
FIG. 1 is an enlarged schematic cross-sectional view illustrating a part of a catheter of the disclosed embodiments.

FIG. 1 is an enlarged schematic cross-sectional view illustrating a part of a catheter of the disclosed embodiments. As illustrated in FIG. 1, a catheter 11 generally includes a hollow shaft 21, a coil body 31, a cover member 41, and a distal tip 51.

The hollow shaft 21 is configured to receive, inside thereof, a guide wire placed in advance in a body cavity such as a blood vessel, for example. The hollow shaft 21 has a tip part P, the outer diameter of which decreases stepwise along the distal direction. The tip part P has a small diameter portion 21a that is a distalmost portion of the tip part P, a large diameter portion 21b having a larger outer diameter than the small diameter portion 21a and located at the proximal end side of the small diameter portion 21a in the axial direction, and a tapered portion 21c that is continuous with the small diameter portion 21a and the large diameter portion 21b and gradually increases in diameter from the small diameter portion 21a toward the large diameter portion 21b.

Specifically, as illustrated in FIG. 1, the hollow shaft 21 has, for example, a lumen 61 into which a guide wire is inserted and that extends along the axial direction in a substantially central portion of a cross section taken perpendicular to the longitudinal axis of the hollow shaft 21, and has the small diameter portion 21a that is a distalmost portion of the tip part P, the tapered portion 21c that is continuous with a proximal end of the small diameter portion 21a and gradually increases in diameter toward the large diameter portion 21b described later, and the large diameter portion 21b that is continuous with a proximal end of the tapered portion 21c. A connector (not illustrated) is connected to an end portion of the hollow shaft 21 in the proximal direction, and various procedures are performed through the connector.

As for the length of each part of the hollow shaft 21 in the axial direction, the length of the entire hollow shaft 21 may be 1350 to 1550 mm, the length of the small diameter portion 21a may be 2 to 10 mm, and the length of the tapered portion 21c may be 2 to 30 mm. As for the outer diameter of each part of the hollow shaft 21, the outer diameter of the small diameter portion 21a may be 0.45 to 0.60 mm, and the outer diameter of the large diameter portion 21b may be 0.50 to 0.65 mm. The inner diameter of the hollow shaft 21 (the diameter of the lumen 61) may be 0.36 to 0.46 mm.

As an example of the catheter 11 according to the present embodiment, a catheter is exemplified in which the large diameter portion 21b is continuous up to the end portion of the hollow shaft 21 in the proximal direction, the length of each part of the hollow shaft 21 in the axial direction is 1550 mm for the entire hollow shaft 21, 5 mm for the small diameter portion 21a, and 10 mm for the tapered portion 21c, the outer diameter is 0.47 mm for the small diameter portion 21a and 0.62 mm for the large diameter portion 21b, and the inner diameter (the diameter of the lumen 61) is 0.38 mm.

Since the hollow shaft 21 is inserted into a body cavity such as a blood vessel, it is preferable that the material of the hollow shaft 21 has antithrombogenicity, flexibility, and biocompatibility. For example, it is possible to employ, as a material of the hollow shaft 21, a resin material such as a polyamide resin, polyolefin resin, polyester resin, polyurethane resin, silicone resin, fluororesin, or the like, or a metal material such as a hypotube or the like. Among these, from the viewpoint of improving the slidability of the guide wire or the like inserted into the lumen 61, a fluororesin is preferable, and polytetrafluoroethylene (PTFE) is more preferable.

Figure 2:
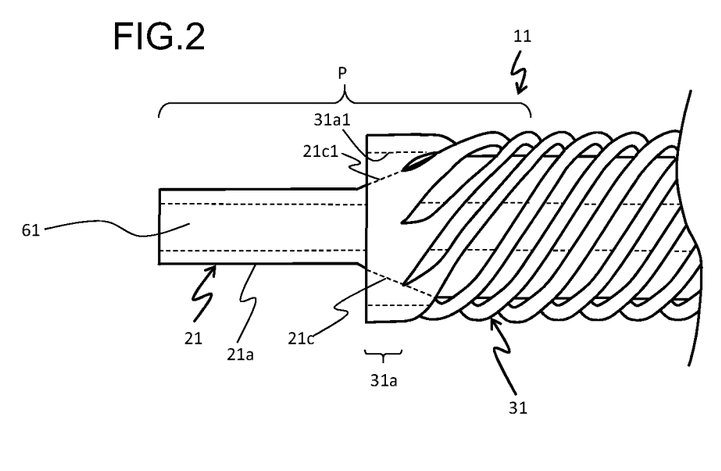
FIG. 2 is an enlarged schematic side view illustrating a hollow shaft and a coil body of FIG. 1.

The coil body 31 has an effect of reinforcing the hollow shaft 21, enhancing the torquability, and the like. As illustrated in FIG. 2, the coil body 31 is wound to cover the outer periphery of the hollow shaft 21, and has a substantially cylindrical joint part 31a at which an end portion of the coil body 31 in the distal direction is joined in the circumferential direction. The joint part 31a is located over the tapered portion 21c and/or the small diameter portion 21a along the axial direction of the hollow shaft 21.

The coil body 31 may be a multi-thread coil body made of multiple wires, or a single-thread coil body made of a single solid wire. As for the single-thread coil body, for example, a wire or the like having a diameter of 0.030 to 0.120 mm can be employed. On the other hand, as for the multi-thread coil body, it may be, for example, a coil body in which 3 to 12 wires having a diameter of 0.010 to 0.120 mm are wound into a hollow twisted wire. Among these, the coil body 31 is preferably a multi-thread coil body. This makes it possible to improve the torquability and the steerability of the catheter 11 while ensuring the ability to track a body cavity when the catheter 11 advances into the body cavity.

The material of the wire for forming the coil body 31 is not particularly limited as long as the material has antithrombogenicity and biocompatibility along with flexibility. For example, stainless steel such as SUS304, SUS316, or the like; a superelastic alloy such as a Ni—Ti alloy or the like; or a metal such as gold, platinum, tungsten, a cobalt chromium alloy, or the like can be employed.

The method of forming the joint part 31a is not particularly limited. For example, a method in which an end portion of the wire in the distal direction of the coil body 31 is irradiated with laser light to be heated and melted, and the end portion is then connected in the circumferential direction to form a substantially cylindrical shape, or a method in which a metal brazing material such as an Sn—Pb alloy, Pb—Ag alloy, Sn—Ag alloy, Au—Sn alloy, or the like is used, and the above-described end portion of the wire is connected in the circumferential direction by brazing to form a substantially cylindrical shape can be employed.

The present embodiment exemplifies a catheter 11 having a multi-thread coil body 31 in which ten wires made of SUS304 and having a diameter of 0.090 mm are twisted together, and the distal end of the twisted wire is joined in the circumferential direction to form a substantially cylindrical shape.

Here, in the catheter 11, in a state in which the hollow shaft 21 extends substantially linearly, the distance between an inner peripheral surface of the joint part 31a and the outer peripheral surfaces of the tapered portion 21c and/or the small diameter portion 21a increases along the distal direction. In the present embodiment, the joint part 31a is located to cover the tapered portion 21c, and the distance between the inner peripheral surface 31a1 of the joint part 31a and the outer peripheral surface 21c1 of the tapered portion 21c increases linearly along the distal direction.

The outer diameter of the joint part 31a is preferably constant. As a result, it is possible to prevent the joint part 31a from bulging (becoming bulky) and ensure the flexibility of the tip part of the catheter 11, and thus reduce the size of the catheter 11.

The cover member 41 is provided on the outer periphery of the hollow shaft 21 and covers the coil body 31, and thus fixes the coil body 31 to the outer periphery of the hollow shaft 21.

The material of the cover member 41 preferably has antithrombogenicity, flexibility and biocompatibility, and for example, a resin such as a polyamide, polyamide elastomer, polyester, polyester elastomer, polyurethane, polyurethane elastomer, or the like can be employed.

As a method of forming the cover member 41, for example, it is possible to employ a method of using an extruder and covering the coil body 31 arranged on the outer periphery of the hollow shaft 21 with a thermoplastic resin such as a polyamide or the like.

The distal tip 51 is provided to cover at least a part of the outer periphery of the tip part P of the hollow shaft 21. Specifically, to enable the catheter 11 to smoothly advance in a body cavity such as a blood vessel and easily pass through a hard lesion such as a calcified lesion, it is possible, for example, to form the distal tip 51 in a spire shape, a substantially truncated cone shape (see FIG. 1), or the like in which the diameter decreases along the distal direction. The end portion of the distal tip 51 in the proximal direction is provided so that a part of the distal tip 51 is sandwiched between the joint part 31a and the hollow shaft 21 and grips them.

The material of the distal tip 51 may be softer than the material of the hollow shaft 21. Depending on the hardness of the hollow shaft 21, it is preferable to use a resin material such as polyurethane, polyurethane elastomer, or the like as the material of the distal tip 51.

As a result of the above-described configuration of the distal tip 51, the flexibility of the hollow shaft 21 is not hindered, and because of the strong joining between the distal tip 51 and the hollow shaft 21, it is possible to prevent the distal tip 51 from coming off the hollow shaft 21.

Figure 3:
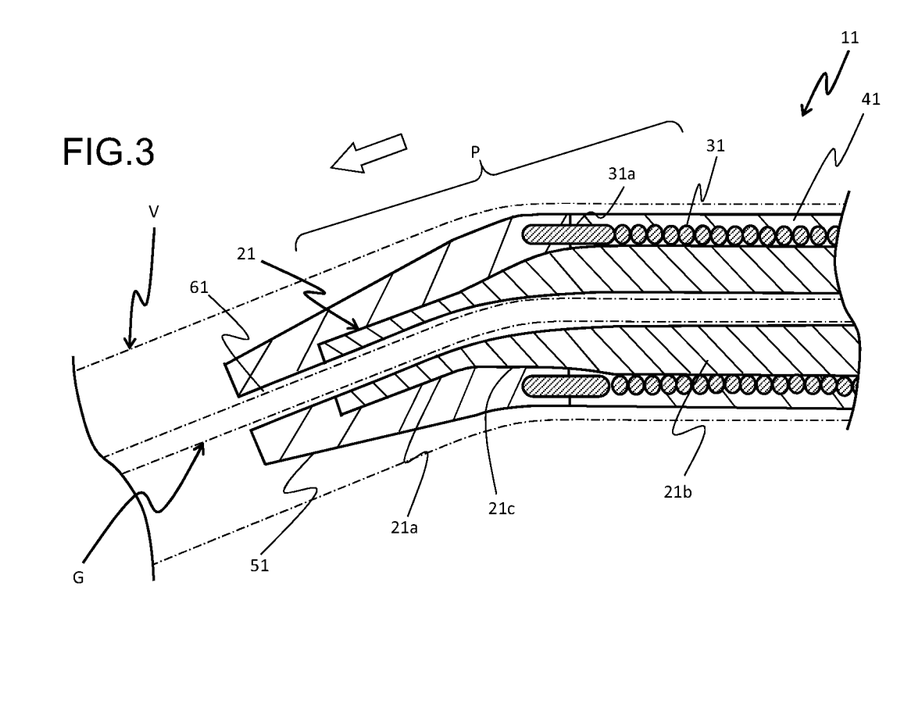
FIG. 3 is a schematic cross-sectional view illustrating an example of a usage state of a catheter illustrated in FIG. 1.

It is possible to use the catheter 11 in the same manner as a known catheter. For example, as illustrated in FIG. 3, after one end (the distal end) of the guide wire G is inserted into the blood vessel V in advance and then advanced up to the site to be treated, the other end (the proximal end) of the guide wire G that is exposed to the outside of the body is inserted into an opening of the lumen 61 of the distal tip 51 of the catheter 11. Next, the catheter 11 is inserted into the blood vessel V, and is pushed along the guide wire G up to the site to be treated in the blood vessel V to perform a predetermined treatment.

As described above, the catheter 11 has the above-described configuration, which makes it possible to curve the tip part P of the hollow shaft 21 within a wide range while preventing unwinding of the coil body 31, and as a result, it is possible to improve the ability to track a curved body cavity when the catheter 11 advances into the curved body cavity.

Figure 5:
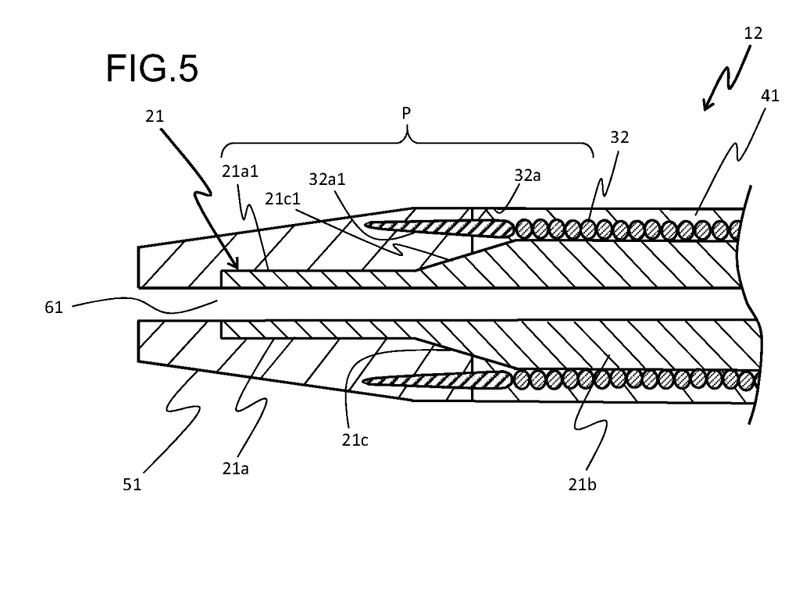
FIG. 5 is an enlarged schematic cross-sectional view illustrating a part of a catheter of the disclosed embodiments.

FIG. 5 is an enlarged schematic cross-sectional view illustrating a part of a catheter of the disclosed embodiments. As illustrated in FIG. 5, a catheter 12 generally includes the hollow shaft 21, a coil body 32, the cover member 41, and the distal tip 51. The shape of the coil body 32 of the catheter 12 is different from that of the coil body 31 of the catheter 11. The configuration other than the shape of the coil body 32 is the same as that of the catheter 11, and therefore, the same parts are designated by the same reference numerals and detailed description thereof will be omitted.

The coil body 32 is wound to cover the outer periphery of the hollow shaft 21, and has a substantially cylindrical joint part 32a at which an end portion of the coil body 32 in the distal direction is joined in the circumferential direction. The thickness of the joint part 32a decreases gradually along the distal direction. Specifically, as illustrated in FIG. 5, the joint part 32a of the catheter 12 has an outer diameter that is constant in the axial direction, and the thickness of the joint part 32a linearly decreases along the distal direction, and as the thickness decreases, the inner diameter of an inner peripheral surface 32a1 of the joint part 32a gradually increases along the distal direction.

The joint part 32a according to the present embodiment is located over the tapered portion 21c and the small diameter portion 21a along the axial direction of the hollow shaft 21, and in a state in which the hollow shaft 21 extends substantially linearly, the distance between the inner peripheral surface 32a1 of the joint part 32a and the outer peripheral surfaces 21c1 and 21a1 of the tapered portion 21c and the small diameter portion 21a, respectively, increases along the distal direction.

As described above, in the catheter 12, the thickness of the joint part 32a decreases gradually along the distal direction, and therefore, as the thickness decreases, it becomes possible to prevent the joint part 32a from becoming bulky, and because of the reduction in size of the catheter 12, it is possible to improve the ability to track a curved body cavity when the catheter 12 advances into the curved body cavity.

The present invention is not limited to the configuration of the above-described embodiments, but is indicated by the claims, and is intended to include all modifications within meanings and the scope equivalent to the claims.

For example, in the above-described embodiments, the catheters 11 and 12 in which the joint parts 31a and 32a are located at least over the tapered portion 21c along the axial direction of the hollow shaft 21 have been described. However, it is only required that the joint part is located over at least one of the tapered portion and the small diameter portion, and thus, for example, a catheter in which the joint part is located only over the small diameter portion is within the scope intended by the present disclosure.

Figure 4:
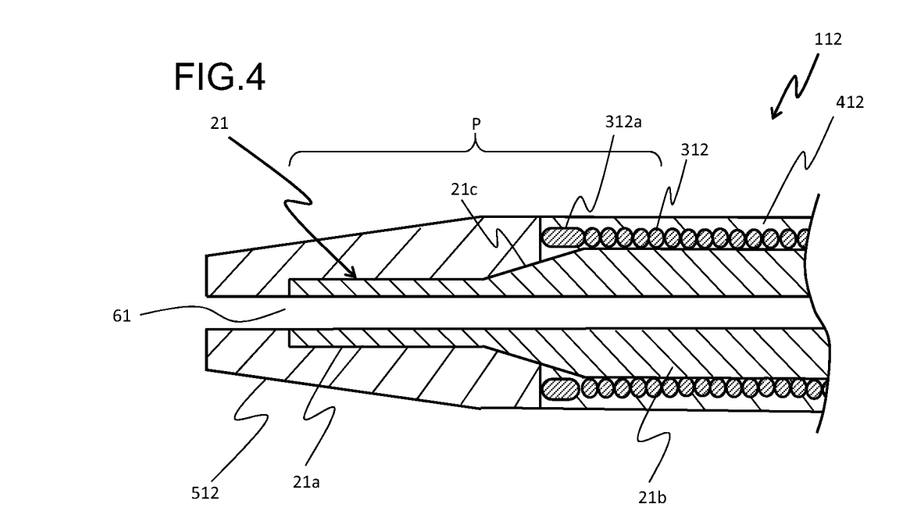
FIG. 4 is a schematic cross-sectional view illustrating a catheter of the disclosed embodiments.
Figure 6:
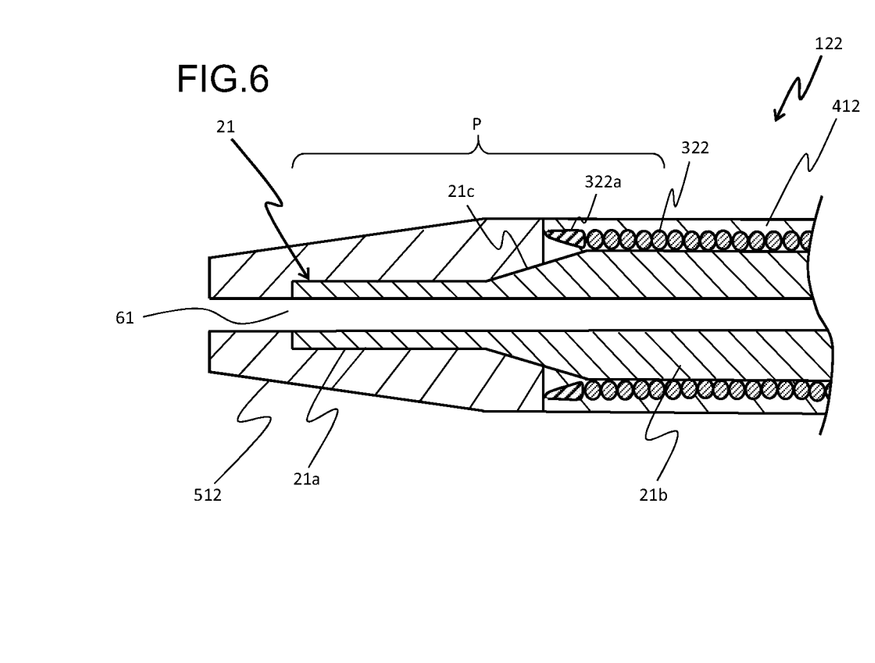
FIG. 6 is a schematic cross-sectional view illustrating a catheter of the disclosed embodiments.

Further, in the above-described embodiments, the catheters 11 and 12 include the cover member 41 that covers a part of the joint parts 31a and 32a (a part of the coil bodies 31 and 32), and a part of the distal tip 51 is sandwiched between the joint part 31a and the hollow shaft 21 and grips them (see FIGS. 1 and 5). However, for example, as illustrated in FIGS. 4 and 6, catheters 112 and 122 may be employed in which the entire joint parts 312a and 322a (including the entire coil bodies 312 and 322) are covered with the cover member 412, and the distal tip 512 abuts the cover member 412 but is not sandwiched between the joint part 312a and the hollow shaft 21.

Further, in the above-described embodiments, the catheters 11 and 12 in which the coil bodies 31 and 32 are fixed to the hollow shaft 21 by the cover member 41 have been described. However, for example, a catheter in which fixing is performed by another method, such as a catheter in which the coil body and the hollow shaft are brazed by using a brazing material may be employed.

Further, in the catheter 12, the outer diameter of the joint part 32a is constant. However, for example, a trumpet-shaped catheter in which the outer diameter of the joint part increases along the distal direction may be employed.

The invention claimed is:
1. A catheter comprising:
   a hollow shaft that includes a distal tip part comprising:
      a small diameter portion that is a distalmost portion of the distal tip part,
      a large diameter portion having a larger outer diameter than the small diameter portion and located at a proximal side of the small diameter portion in an axial direction of the hollow shaft, and
      a tapered portion that is continuous with the small diameter portion and the large diameter portion and that gradually increases in diameter from the small diameter portion toward the large diameter portion; and
   a coil body disposed on an outer periphery of the hollow shaft, wherein:
the distal tip part of the hollow shaft decreases in wall thickness toward the distalmost portion of the distal tip part;
a distal end portion of the coil body in the axial direction is joined in a circumferential direction to form a joint part;
the joint part is located over the tapered portion and/or the small diameter portion along the axial direction; and
in a state in which the hollow shaft extends linearly, a distance in a radial direction of the hollow shaft between an inner peripheral surface of the joint part and an outer peripheral surface of the tapered portion and/or an outer peripheral surface of the small diameter portion increases toward the distalmost portion of the distal tip part of the hollow shaft in the axial direction.

2. The catheter according to claim 1, wherein a thickness of the joint part decreases toward a distal end of the joint part.

3. The catheter according to claim 2, wherein an outer diameter of the joint part is constant.

4. The catheter according to claim 2, wherein an inner diameter of the joint part increases toward a distal end of the joint part.

5. The catheter according to claim 1, wherein the coil body is a multi-thread coil body.

6. The catheter according to claim 1, wherein the coil body is a single-thread coil body.

7. The catheter according to claim 1, further comprising a distal tip that covers at least a part of an outer periphery of the distal tip part of the hollow shaft.

8. The catheter according to claim 7, wherein the distal tip is formed of a material that is softer than a material of the hollow shaft.

9. The catheter according to claim 7, wherein a part of the distal tip is sandwiched between the joint part and the hollow shaft and grips the joint part and the hollow shaft.

10. The catheter according to claim 1, further comprising a cover member covering at least a part of the coil body and provided on the outer periphery of the hollow shaft.

11. The catheter according to claim 10, wherein the cover member covers at least a part of the joint part.

12. The catheter according to claim 10, wherein the cover member covers the entire joint part.

13. The catheter according to claim 10, wherein the cover member covers the entire coil body.

14. A catheter comprising:
a hollow shaft that includes a distal tip part comprising:
a small diameter portion that is a distalmost portion of the distal tip part,
a large diameter portion having a larger outer diameter than the small diameter portion and located at a proximal side of the small diameter portion in an axial direction of the hollow shaft, and
a tapered portion that is continuous with the small diameter portion and the large diameter portion and that gradually increases in diameter from the small diameter portion toward the large diameter portion;
a coil body disposed on an outer periphery of the hollow shaft; and
a distal tip that covers at least a part of an outer periphery of the distal tip part of the hollow shaft, the distal tip being formed of a material that is softer than a material of the hollow shaft,
wherein:
a distal end portion of the coil body in the axial direction is joined in a circumferential direction to form a joint part;
the joint part is located over the tapered portion and/or the small diameter portion along the axial direction; and
in a state in which the hollow shaft extends linearly, a distance in a radial direction of the hollow shaft between an inner peripheral surface of the joint part and an outer peripheral surface of the tapered portion and/or an outer peripheral surface of the small diameter portion increases toward the distalmost portion of the distal tip part of the hollow shaft in the axial direction.

15. The catheter according to claim 14, wherein the distal tip is formed of a resin material.

* * * * *